United States Patent
DuBourdieu et al.

(10) Patent No.: US 11,357,802 B2
(45) Date of Patent: Jun. 14, 2022

(54) ORAL DELIVERY COMPOSITIONS FOR IMPROVED GUT BARRIER PROTECTION AND IMMUNITY IN MAMMALS

(71) Applicant: Vets Plus, Inc., Menomonie, WI (US)

(72) Inventors: Daniel J. DuBourdieu, Limerick, ME (US); Rajiv Lall, Menomonie, WI (US); Ajay Srivastava, Menomonie, WI (US)

(73) Assignee: Vets Plus, Inc., Menomonie, WI (US)

( * ) Notice: Subject to any disclaimer, the term of this patent is extended or adjusted under 35 U.S.C. 154(b) by 544 days.

(21) Appl. No.: 16/402,008

(22) Filed: May 2, 2019

(65) Prior Publication Data
US 2019/0336546 A1    Nov. 7, 2019

Related U.S. Application Data

(60) Provisional application No. 62/665,900, filed on May 2, 2018.

(51) Int. Cl.
| | | |
|---|---|---|
| A61K 35/742 | (2015.01) | |
| A61K 9/00 | (2006.01) | |
| A61P 1/00 | (2006.01) | |
| A23L 33/135 | (2016.01) | |
| A23L 33/155 | (2016.01) | |
| A23L 33/175 | (2016.01) | |
| A61K 31/375 | (2006.01) | |
| A61K 31/07 | (2006.01) | |
| A61K 31/198 | (2006.01) | |
| A61K 31/355 | (2006.01) | |

(52) U.S. Cl.
CPC .......... *A61K 35/742* (2013.01); *A23L 33/135* (2016.08); *A23L 33/155* (2016.08); *A23L 33/175* (2016.08); *A61K 9/0056* (2013.01); *A61K 31/07* (2013.01); *A61K 31/198* (2013.01); *A61K 31/375* (2013.01); *A61P 1/00* (2018.01); *A23V 2002/00* (2013.01); *A23V 2200/3202* (2013.01); *A23V 2200/3204* (2013.01); *A23V 2250/0606* (2013.01); *A23V 2250/5034* (2013.01); *A23V 2250/702* (2013.01); *A23V 2250/708* (2013.01); *A23V 2250/712* (2013.01); *A61K 31/355* (2013.01)

(58) Field of Classification Search
CPC .................................................. A61K 35/742
See application file for complete search history.

(56) References Cited

U.S. PATENT DOCUMENTS

2013/0171204 A1    7/2013    Dubourdieu et al.

OTHER PUBLICATIONS

English machine translation of Yang et al., CN 103798553 A, 2014.*

(Continued)

*Primary Examiner* — Rosanne Kosson
(74) *Attorney, Agent, or Firm* — Daniel A. Blasiole; DeWitt LLP

(57) ABSTRACT

Compositions containing probiotics and a nitric oxide precursor such as L-arginine to enhance nitric oxide production in animals and methods for improving immunity, gut barrier functions, and gut health and treating gastroenteritis and mucositis in animals using same.

17 Claims, 1 Drawing Sheet

(56) References Cited

OTHER PUBLICATIONS

Flora Choice—daily. Gut support. For support of daily and long term gut health. Powder for Cats & Dogs. Product Detail Sheet: Mar. 18, 2019. Clinics Choice, Acworth, GA 30101. Sold: Mar. 27, 2019.

Recov Choice. Energy support. Energy support. Helps maintain electrolyte balance. Manages the nutrient uptake. Gel for Dogs. Product Detail Sheet: Mar. 18, 2019. Clinics Choice, Acworth, GA 30101. Sold: Mar. 27, 2019.

Blijlevenes et al., Mucositis: from febrile neutropenia to febrile mucositis, *Journal of Antimicrobial Chemotherapy*, (2009) 63, Suppl. 1, i36-i40.

Flickinger et al., Nutrient digestibilities, microbial populations, and protein catabolities as affected by fructan supplementation of dog diets, *j. Anim. Sci.* (2003), 81:2008-2018.

Herstad et al., Effects of a probiotic intervention in acute canine gastroenterities—a controlled clinical trial, *J. Small Anim, Pract.* (2010), 51(1):34-8.

Ishizaka et al., Oral Administration of Fermented Probiotics Improves the Condition of Feces in Adult Horses, *J. Equine Sci.*, (2014), vol. 25, No. 4, pp. 65-72.

Kochar et al., Beneficial effects of L-arginine against diabetes-induced oxidative stress in gastrointestinal tissues in rats, *Phramacol. Rep.*, (2009), 61(4):665-72 (Abstract only).

Kochar et al., Nitric Oxide and the Gastrointestinal Tract, *International Journal of Pharmacology*, (2011), 7(1):31-39.

Kogut, M.H., The gut microbiota and host innate immunity: Regulators of host metabolism diseases in poultry, *J. Appl. Polut. Res.*, (2013), 22:637-646.

Leocádio et al., L-Arginine pretreatment reduces intestinal mucositis as induced by 5-FU in mice, *Nutr. Cancer*, (2015), 67(3):486-93.

Mansourian et al., Fecal-Derived Phenol Induces Egg-Laying Aversion in *Drosophila*, *Current Biology*, (2016), 26, 2762-2769.

Popovic et al., Arginine and Immunity[1-3], *The Journal of Nutrition*, (2007), 137: 1681S-1686S.

Raul et al., Beneficial Effects of L-Arginine on Intestinal Epithelial Restitution after Ischemic Damage in Rats, *Digestion*, (1995), 56(5):500-5.

Rishi et al., Effect of Lactobacillus plantarum and L-Arginine against endotoxin-induced liver injury in a rat model. *Lide Sci.*, (2011), 89(23-24): 847-53.

Sauter et al., Effects of probiotica bacteria in dogs with food responsive diarrhea treated with an elimination diet, *J. Anim, Phsiol. Anim. Nutr (Berl)*, (2006), 90(7-8):269-77.

Suzuki et al., Effect of *Bacillus subtillis* C-3102 Intakes on the Composition and Metabolic Activity of Fecal Microflora of Humans, (2004), Fuchinobe, Sagamihara 229-0006 Japan.

Umanthe et al., Gastrointestinal dysfunction in diabetic rats relates with a decline in tissue 1-arginine content and consequent low levels of nitric oxide, *Nitric Oxide*, (2009), vol. 20, Issue 2, pp. 129-133.

Wang et al., Bacterial Flavodoxins Support Nitric Oxide Production by *Bacillus subtilis* Nitric-oxide Synthase, *The Journal of Biological Chemistry*, (2007), vol. 282, No. 4, pp. 2196-2202.

Wapnir et al., L-arginine in low concentration improves rat intestinal water and sodium absorption from oral rehydration solutions, *Gut*, (1997), 40:602-607.

\* cited by examiner

ORAL DELIVERY COMPOSITIONS FOR IMPROVED GUT BARRIER PROTECTION AND IMMUNITY IN MAMMALS

FIELD OF THE INVENTION

The present invention relates to oral treatments for improving immunity, gut barrier functions, and gut health in animals such as mammals.

BACKGROUND

The expression "gut health" has now entered the collective consciousness of animal industries and research. There are many reasons why this has occurred. The gastrointestinal (GI) tract is the largest interface between the external environment and the internal environment of the animal. The GI tract constitutes the major barrier through which molecules can either be absorbed or secreted. The GI tract acts as a physical and immune barrier to pathogens and has the largest residence of immune cells in body. The GI tract is also the natural habitat for a large and dynamic community of microbes that participate and regulate gut and systemic functions. Gut health can be thought of as the ability to perform normal physiological functions and to maintain homeostasis, thereby supporting the gut's ability to withstand infections and non-infectious stressors (Kogut 2013). However, overt disease is not required to affect animal health, as evidenced in subclinical infections.

There are 5 basic components of gut health. These include effective digestion/food absorption, stable microbial population, effective immune status, effective gut barrier, and an effective neuroendocrine system. All of these components of gut health can be disturbed in times of stress to companion animals. Stress can come in many forms, from overt disease to less obvious challenges, such as kenneling for a companion animal. However, the outcome of these stresses typically challenges the GI tract first. A typical result of that stress can be gastroenteritis. It has been a challenge in creating formulations that take into account the various components of gut health that, in turn, help with overall animal health in times of stress.

The current invention is directed to compositions and methods for improving animal health by acting on certain key components of gut health.

SUMMARY OF THE INVENTION

One aspect of the invention is directed an oral ingestible composition for improving gut health in an animal. The oral ingestible composition comprises effective amounts of active ingredients. In preferred versions, the active ingredients comprise a probiotic and a nitric oxide precursor.

The probiotic preferably comprises a spore-forming probiotic. The spore-forming probiotic is preferably present in the oral ingestible composition in spore form. The probiotic preferably comprises a member of the genus *Bacillus*. The probiotic preferably comprises a combination of *Bacillus coagulans, Bacillus licheniformis*, and *Bacillus subtilis*. The probiotic is preferably included in the composition in an amount from about 0.15% w/w to about 15% w/w.

The nitric oxide precursor preferably comprises L-arginine. The nitric oxide precursor is preferably included in the composition in an amount from about 0.015% w/w to about 1.5% w/w.

The oral ingestible composition preferably further comprises an immunomodulator, such as beta glucan, as an additional active ingredient.

The oral ingestible composition preferably further comprises vitamin C, vitamin A, and vitamin E.

The oral ingestible composition preferably further comprises a prebiotic, such as inulin. The oral ingestible composition is preferably in the form of a soft dough composition with the active ingredients evenly distributed throughout or in the form of a dispersible powder.

Another aspect of the invention is directed a method of improving gut health in an animal. The method comprises orally administering an oral ingestible composition of the invention to the animal. The administering is preferably performed in an amount and for a time effective to improve gut health in the animal. Improvements to gut health can include or be indicated by a reduction of phenols present in the feces of the animal, a reduction of indoles in the feces of the animal, a reduction of mucositis, a reduction of gastroenteritis, or any other indicator or outcome of improved gut health.

If the oral ingestible composition is in the form of a dispersible powder, the composition is preferably added to a foodstuff prior to the administering. The foodstuff can be a solid foodstuff, a semi-solid foodstuff, or a liquid foodstuff.

The animal to which the composition is administered is preferably an animal exhibiting detectable signs of stress, an animal suffering from gastroenteritis, and/or an animal suffering from mucositis. The animal is preferably a canine, feline, or human.

In preferred methods, the nitric oxide precursor is L-arginine and is included in the composition in an amount from about 0.015% w/w to about 1.5% w/w, the probiotic is included in the composition in an amount from about 0.15% w/w to about 15% w/w, and the composition is administered to the animal in an amount from about 0.02 g/kg animal body weight/day to about 2 g/kg animal body weight/day for a period of at least two consecutive days.

The composition can be administered in an amount and for a time effective to reduce a value of a parameter selected from the group consisting of phenol concentration and indole concentration in feces of the animal with respect to a value of the parameter in the feces of the animal not administered the oral ingestible composition but otherwise subjected to identical conditions.

Another aspect of the invention is a method of treating gastroenteritis in an animal in need thereof. The method comprises orally administering an oral ingestible composition of the invention to the animal. The administering is preferably performed in an amount and for a time effective to provide at least some alleviation of the gastroenteritis or symptoms thereof in the animal.

Another aspect of the invention is a method of treating mucositis in an animal in need thereof. The method comprises orally administering an oral ingestible composition of the invention to the animal. The administering is preferably performed in an amount and for a time effective to provide at least some alleviation of the mucositis or symptoms thereof in the animal.

The objects and advantages of the invention will appear more fully from the following detailed description of the preferred embodiment of the invention made in conjunction with the accompanying drawings.

DETAILED DESCRIPTION OF THE INVENTION

Figure 1:
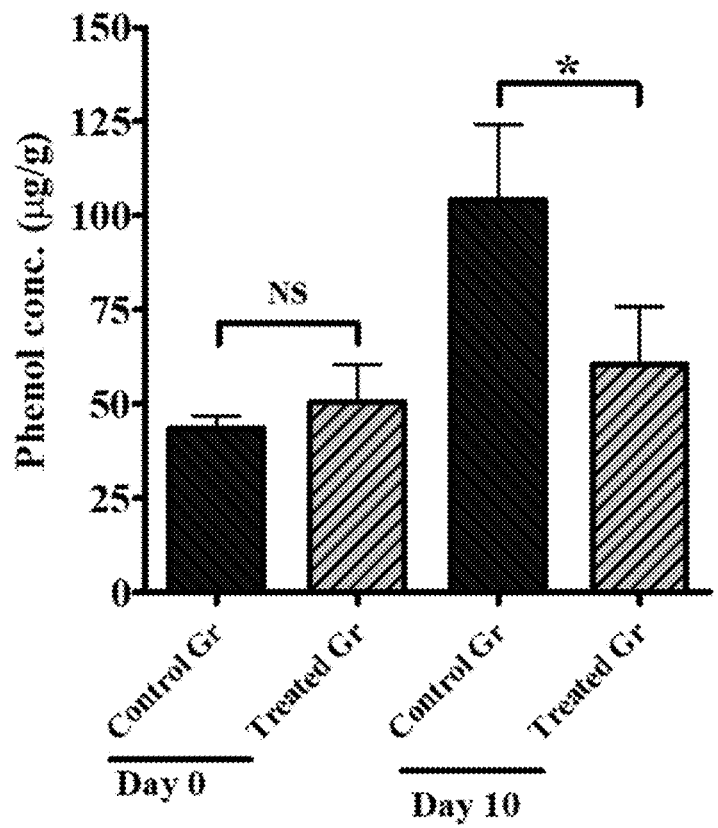
FIG. 1 shows phenol concentrations at days 0 and 10 in the feces of animals fed a high-protein control diet and animals fed a high-protein diet supplemented with a composition of the invention.

One of the components of gut health is a stable intestinal flora. Intestinal flora plays an important role in determining the digestive mechanisms and improving the overall general health in all animals. The digestive system of animals contains billions of bacteria, some of which are beneficial (e.g., probiotics) and some of which are pathogenic. In a normal healthy animal, there is a delicate balance between beneficial and pathogenic bacteria. Normally, beneficial bacteria grow more rapidly than pathogenic bacteria viruses, fungi, and parasites, depriving the pathogens of needed nutrients. Thus, most of the bacteria in the gut are beneficial bacteria. The beneficial bacteria make certain important B-complex vitamins, help improve certain normal digestive processes including fermentation of carbohydrates to lactic acid, reduce blood ammonia levels, stimulate the immune system, and thus lead to a healthy life in many domesticated animals. However, when there is extended stress on the animal, such as during an infection, surgery etc., the whole system is upset, and the delicate balance is lost. The number of beneficial bacteria declines rapidly, and the pathogenic bacteria increase in number several fold. Pathogenic bacteria secrete toxins, which can lead to illness in the animal. This in turn can lead to further stress and further imbalance of the beneficial bacteria. Invasive pathogenic bacteria produce volatile organic compounds such as phenols, indole, and skatole that cause unpleasant odors in feces of mammals. The pathogenic bacteria produce phenols from L-tyrosine found in high protein diets (Mansourian 2016) such as found in meat diets that carnivores consume. The imbalance between beneficial and pathogenic bacteria can be corrected by adding back probiotic bacteria to recolonize the gut.

Once the probiotics have begun to recolonize the gut, they will begin competing with the pathogenic bacteria to bring back the normal balance. Several mechanisms can be responsible for this interaction, including competition for the adherence sites on the epithelial cells lining the GI tract by the beneficial bacteria that crowd out the pathogenic bacteria or competition for nutrients. Other mechanisms include poisoning the pathogenic bacteria with antibiotic-like growth-inhibiting factors such as bacteriocins or hydrogen peroxide production. As the production of toxins from pathogenic bacteria declines with the decline in pathogenic bacteria to tolerable levels, the animal recovers normal appetite and digestion leading to weight gain.

Endogenous nitric oxide regulates mucosal barrier integrity under physiological conditions and counters the increase in mucosal permeability associated with acute pathophysiological states. The potential mechanisms of actions of nitric oxide in companion animals include maintenance of blood flow, inhibition of platelet and leukocyte adhesion, and/or aggregation within the vasculature, modulation of mast cell reactivity, and scavenging of reactive oxygen metabolites such as superoxide. Endogenous nitric oxide production in the body comes from the amino acid L-arginine and other precursor substrates. *Bacillus subtilis* can also produce nitric oxide (Wang 2007). Both constitutive nitric oxide synthase-derived endogenous nitric oxide and exogenous nitric oxide (from nitric oxide donors) can reduce the problems of acute inflammation. The present invention stimulates nitric oxide production from both endogenous and exogenous sources as a way of stimulating gut health which, in turn, maintains animal health.

In companion animals, acute gastroenteritis with vomiting and diarrhea and chronic enteropathies (CE) are common complaints. In addition, stress associated with a kennel environment, traveling, or other stressful situations may cause changes in the gut function that can manifest as poor stool quality and diarrhea. Furthermore, proliferation of pathogenic intestinal bacteria and an abnormal immune response towards the intestinal infections may cause gastrointestinal symptoms including inflammation. One of the characteristics of the intestinal immune system in the gut barrier function is that it defends against pathogens and entry of excessive intestinal microbes. Normally, the mucosal immune system is also responsible for the balance between pro- and anti-inflammatory mediators. This system helps to protect against luminal pathogens, as well as prevent an immune overreaction against harmless luminal antigens (such as beneficial bacteria or food). In certain pathophysiological conditions such as mucositis, this immunological balance is impaired and shifted toward a more pro-inflammatory state, which is caused primarily by the increased activation of effectors immune cells.

Mucositis is a condition better referred to as mucosal barrier injury (MBI) since it is primarily the result of toxicity and is a complex and dynamic pathobiological process manifested throughout the entire digestive tract. A model has been proposed for MBI and consists of four phases. These include inflammatory, epithelial, ulcerative, and healing phases. A variety of factors are involved in causing and modulating MBI including the nature of the conditioning regimen, the elaboration of pro-inflammatory and other cytokines, translocation of the resident microflora and their products, for example, endotoxins across the mucosal barrier or exposure to antimicrobial agents. Gastrointestinal mucositis can be treated with oral rehydration solutions and antidiarrheal medicines, but these drug approaches do not address some of the underlying causes of the problem of the mucosal barrier integrity.

The compositions and methods of the invention can alleviate the problems outlined above by delivering probiotics and nitric oxide precursors to the gut. The present invention principally employs the use of an oral delivery system for the oral administration of stable probiotics with immunomodulator and other components, which together form a synergistic beneficial therapeutic effect on the animal in times of stress. The compositions and methods of the invention provide stable and viable probiotic bacteria to the gut, strengthening gut immunity and gut barrier aspects, while providing additional nitric oxide via exogenous and endogenous sources in a synergistic manner to help maintain normal mucosal barrier integrity. This is done, for example, by combining spore forming probiotics with nitric oxide precursors such as L-arginine and, optionally, immunomodulator. In so doing, the present invention takes into account some of the underlying causes and the symptoms of gastroenteritis and mucositis and other disorders related to mucosal barrier integrity. The exogenous nitric oxide produced by probiotics and the use precursors of endogenous nitric oxide to produce additional nitric oxide help maintain normal mucosal barrier integrity.

The compositions of the invention can include a number of active ingredients. In addition to a probiotic and a nitric oxide precursor, the active ingredients can also optionally include a prebiotic, an immunomodulator, one or more vitamins, and one or more minerals.

The probiotic can comprise one or more probiotics from any of a number of genera. Exemplary genera of probiotics include *Bacillus, Lactobacillus*, and *Bifidobacterium*. Probiotics have also been developed from such genera as *Escherichia, Enterococcus, Bacillus, Propionibacterium*, and *Saccharomyces*.

Preferred probiotics include spore-forming bacteria from the genus *Bacillus*.

Particularly preferred probiotics include a combination *Bacillus subtilis, Bacillus coagulans*, and *Bacillus licheniformis*, preferably in a spore format. The advantage of the combination of *Bacillus* species is that they are active against a wide range of conditions and in a wider range of animal species.

Furthermore, unlike many *Lactobacillus*-type bacteria, the preferred *Bacillus* strains are able to survive the rigors of manufacturing and subsequent passage through the GI tract. This is because the preferred *Bacillus* strains are spore formers that can exist in a desiccated and dehydrated state and thus survive manufacturing and transit of the GI tract. The preferred *Bacillus* strains are surrounded by a natural protective shield, which helps them survive the heat and pressure of manufacturing and the acids and bile of digestion, so they have a far better chance of arriving alive and well in the intestines, where they go to work. On the other hand, the majority of *Lactobacillus*-type probiotics get destroyed upon entry into the stomach. Only the few that can survive would populate the small intestine and prevent colonization of the intestine by harmful bacteria. Furthermore, most, if not all, of *Lactobacillus* and *Bifidobacterium* probiotics are unstable at elevated temperatures above 40° C. and thus require special manufacturing and storage conditions for any kind of extended shelf life in a product. They are also often not good colonizers of the gut. The *Lactobacillus* and *Bifidobacterium* probiotics often are sensitive to bile and acidic conditions in the gut, which helps explain why they have poor viability and survivability in the gut.

The total probiotics in the composition can be included in the composition in a total amount from about 0.005% w/w to about 45% w/w, such as from about 0.15% w/w to about 15% w/w or from about 0.5% w/w to about 4.5% w/w. Each individual probiotic (e.g., each of *Bacillus subtilis, Bacillus coagulans*, and *Bacillus licheniformis*) can be included in the composition in an amount from about 0.015% w/w to about 15% w/w, such as from about 0.05% w/w to about 5% w/w or from about 0.15% w/w to about 1.5% w/w.

When the composition is formulated in a single dosage form (such as a single-serving viscoelastic mass as in Example 3), each individual probiotic can be included in an amount of from about 1 million to about 400 billion colony forming units (CFU) per dose, such as from about 100 million to about 200 billion CFU or from about 30 billion to about 70 billion. This gives about a total of about 100 billion to about 200 billion CFU per dose of all of the bacteria in the composition.

The nitric oxide precursor can include any compound capable of being converted to nitric oxide in vivo, either by the animal itself or by a microorganism harbored by the animal.

Exemplary nitric oxide precursors include L-arginine, N-w-hydroxy-L-arginine, ornithine, ornithine alpha-ketoglutarate, citrulline, and agmatine, among others. A preferred nitric oxide precursor is L-arginine.

The present invention helps regulate mucosal barrier integrity by working in a synergistic manner to produce nitric oxide under physiological conditions and counter the increase in mucosal permeability associated with acute pathophysiological states. L-arginine, N-w-hydroxy-L-arginine, ornithine, ornithine alpha-ketoglutarate, citrulline, and agmatine are precursors of nitric oxide in animals. Certain probiotic bacteria such as *Bacillus subtilis* also produce nitric oxide (Wang 2007). By adding *Bacillus subtilis* along with the nitric oxide precursor, a synergistic effect can occur to produce nitric oxide and, in turn, help maintain normal mucosal integrity in times of stress in companion animals. This synergistic effect allows for one of the important aspects of gut health to be achieved.

The amount of the nitric oxide precursor included in the compositions of the invention can be adapted to the specific needs of the target animal. As an example, the nitric oxide precursor may be included in an amount from about 0.001% w/w to about 10.0% w/w of the composition, such as from about 0.0005% w/w to about 4.5% w/w, from about 0.015% w/w to about 1.5% w/w, or from about 0.05% w/w to about 0.45% w/w.

The compositions of the invention can optionally include a prebiotic. The probiotic bacteria work best and offer superior gut health benefits when combined with a prebiotic. Exemplary prebiotics include soluble fibers such as fructo-oligosaccharides inulin. These fibers serve as food to the probiotic bacteria and help the probiotics thrive once they reach the gut, thus enabling a key parameter of gut health for a providing a stable microbial population in times of stress. The amount of the prebiotic included in the compositions of the invention can be adapted to the specific needs of the target animal. As an example, the prebiotic may be included in an amount of from about 0.001% to about 10.0% w/w of the composition, such as from about 0.015% w/w to about 15% w/w, from about 0.05% w/w to about 5% w/w, or from about 0.15% w/w to about 1.5% w/w.

The compositions of the invention can optionally include an immunomodulator. A preferred immunomodulator is beta glucan. Beta glucan is a preferred immunomodulator that helps stimulate the immune system in times of stress. The amount of the beta glucan included in the viscoelastic mass of the invention can be adapted to the specific needs of the target animal. As an example, beta glucan may be included in an amount from about 0.001% w/w to about 10.0% w/w of the composition, such as from about 0.0075% w/w to about 7.5% w/w, from about 0.025% w/w to about 2.5% w/w, or from about 0.075% w/w to about 0.75% w/w. Other immunomodulators that can work in the present invention are from natural herbal sources and include garlic, turmeric, and tea. These are Association American Feed Control Official (AFFCO)-approved ingredients. Vitamins A, C, and E are suitable immunomodulators. These are also all AFFCO approved ingredients. Vitamins A, C, and E can each be present in the composition in an amount from about 0.003% w/w to about 3% w/w, such as from about 0.01% w/w to about 1% w/w or from about 0.03% w/w to about 0.3% w/w.

The compositions of the invention can optionally include one or more vitamins. Vitamins often work in conjunction with minerals and enzymes to assure normal digestion, reproduction, muscle and bone growth and function, healthy skin and hair, clotting of blood, and the use of fats, proteins, and carbohydrates by the body. For example, vitamin E isomers (mixed tocopherols) are antioxidants that help protect animals from free radical damage. Vitamin deficiencies can occur in an animal if poor quality food is provided to the animal. Vitamin deficiencies can also occur if an animal is under stress. Ill or recovering animals that may have a poor appetite typically need a vitamin supplement since they are not receiving their daily requirements through the food they eat. Animals in other situations such as stress from travel, showing, training, hunting, breeding, or lactation can also benefit from vitamin supplementation. Older animals can also benefit from vitamin supplementation. Older animals tend to absorb fewer vitamins, minerals, and electrolytes through the intestinal tract, and lose more of them through the kidneys and urinary tract. Also, some older animals eat less (due to conditions such as oral disease) and may not receive their daily needs of vitamins and minerals. These same old animals are often the ones that will also be given solid medications to treat other conditions. Another issue that may increase the need for vitamin supplementation in animals is that commercial feeds typically involve a heating process that can destroy vitamins present in the feed. Preferred compositions of the invention do not involve heat for manufacture and are therefore able to provide vitamins that are not degraded.

Any vitamin known in the art may be included in the composition of the present invention. Particular vitamins may be provided according to the nutritional requirements of the target animal. Suitable vitamins include both water soluble and/or fat-soluble vitamins. Exemplary water-soluble vitamins include any or all of the B vitamins (Vitamin $B_1$, $B_2$, $B_3$, $B_4$, $B_5$, $B_6$, $B_7$, $B_8$, $B_9$, $B_{10}$, $B_{11}$, and $B_{12}$) and/or Vitamin C (ascorbic acid). Exemplary fat-soluble vitamins include Vitamin A, Vitamin D, Vitamin E, and Vitamin K. As stated above, vitamins A, C, and E also function as immunomodulators. The fat-soluble vitamins may be provided as an element of oils utilized in the present invention, such as, for example, canola oil, corn oil, soybean oil, and vegetable oil. The amount of the vitamins included in the compositions of the invention can be adapted to the specific needs of the target animal. As an example, each vitamin may be included in the composition in an amount of from about 0.001% to about 10.0% w/w, such as from about 0.003% w/w to about 3% w/w, from about 0.01% w/w to about 1% w/w, or from about 0.03% w/w to about 0.3% w/w.

The compositions of the invention can optionally include minerals. Minerals play important roles in many biochemical functions in the body. Deficiencies of minerals can lead to problems in the immune system. However, supplementation of zinc and copper can help correct these problems. As absorption of chelated minerals to amino acids or other substances is enhanced, this invention uses chelated minerals. Preferred minerals include chelated copper, zinc, manganese, and molybdenum to benefit the immune system. A preferred concentration of copper is from about 0.1 mg/kilogram to about 2 mg/kilogram; for zinc is from about 100 mg/kilogram to about 300 mg/kilogram; and for manganese is from about 0.05 mg/kilogram to about 0.2 mg/kilogram.

A number of oral delivery systems are available to deliver the active ingredients orally to animals. These include pastes, gels, pills, tablets, boluses, powders, and hard or soft chew formats. Preferred delivery systems include soft chew formats and powder formats. The soft chew formats can be formulated to be administered as single-serve "treats." The powder formats can be formulated to be administered as is or added to a foodstuff prior to administering. "Foodstuff" refers to any ingestible or drinkable substance typically consumed by an animal to contribute or meet the animal's daily caloric and hydration needs. The foodstuff can be a solid foodstuff (e.g., animal chow), a semi-solid foodstuff (e.g., gelatin, yogurt, pudding), or a liquid foodstuff (e.g., water, milk). The active ingredients are preferably evenly distributed (e.g., thoroughly mixed) throughout the delivery system.

The powder delivery systems can include anti-caking agents (e.g., TIXOSIL-brand silica (Solvay, Brussels, Belgium), dicalcium phosphate anhydrous) to maintain a powder consistency, flavorings or taste enhancers (e.g., maltodextrin, poultry liver powder, powdered sugar, and sodium chloride) to improve palatability, and other additional components.

The soft chew delivery system can comprise a viscoelastic mass. The viscoelastic mass is an edible, dough-like composition. An exemplary soft chew delivery system can include, for example, a base powder, lecithin, glycerol, molasses, sugar, starch, mixed tocopherols, sodium chloride, preservatives and/or water mixed together to form a soft dough composition and extruded.

The base powder generally provides structural integrity to the mass. The base powder may comprise a plant powder, an animal powder, or both a plant and an animal powder. Plant powders are powders derived from plants, such as flours or other powders. The flours may be whole flours or flours which have had fractions, such as the germ fraction or the husk fraction, removed. Non-limiting examples of suitable plant powders include soy flour, wheat flour, whole wheat flour, whole wheat fine flour, wheat feed flour, wheat gluten, pre-gel wheat flour, soy protein concentrate, oat flour or powder, barley powder or flour, brown rice flour or powder, dried whey powder, carrot powder, cherry powder, pineapple powder, and alfalfa herb powder. Animal powders are powders derived from animals and can include dehydrated meat byproducts, such as liver powder. In a preferred version of the invention, the base powder comprises an animal powder and a plant flour, which can be mixed with a fluid lubricant. The powder is preferably included in an amount of from about 0.01% to about 50% w/w of the delivery system.

The delivery system may include a starch. As used herein, "starch" refers to any substance comprised of more than about 80%, 90%, 95%, or even 99% amylase and amylopectin by weight. Starches from various sources are known in the art. Suitable starches can be obtained from tuberous foodstuffs, such as potatoes, tapioca, and the like. Other suitable starches can be obtained upon grinding cereal grains such as corn, oats, wheat, milo, barley, rice, and others. The starch may be included in an amount of from about 0.01% to about 2% w/w of the delivery system, such as from about 1% to about 15% w/w or from about 5% to about 9% w/w of the delivery system.

The composition may include an emulsifier. Suitable emulsifiers include nonionic surfactants, such as polyoxyethylated castor oil, polyoxyethylated sorbitan monooleate, sorbitan monostearate, ethyl alcohol, glycerol monostearate, polyoxyethylene stearate, and alkylphenol polyglycol ethers; ampholytic surfactants, such as disodium N-lauryl-B-iminodipropionate and lecithin; and anionic surfactants, such as sodium lauryl sulphate, fatty alcohol ether sulphates, and mono/dialkyl polyglycol ether orthophosphoric ester monoethanolamine salt. A preferred emulsifier is lecithin, such as soy lecithin. The emulsifier may be included in an amount of from about 0.01% to about 20% w/w of the delivery system, such as from about 4% to about 16% w/w or from about 6% to about 10% w/w of the delivery system.

In order to provide an edible soft chew, the composition preferably includes a softening agent. Examples of suitable softening agents include glycerol and propylene glycol, wetting agents such as cetyl alcohol and glycerol monostearate, and other humectants. Glycerin is a preferred softening agent and can maintain the softness of the composition over the shelf life of the product. The softening agent may be included in an amount from about 0.01% to about 50% w/w of the delivery system, such as from about 5% to about 25% w/w or from about 9% to about 14% w/w of the delivery system.

A flavoring is preferably included in the composition to enhance the palatability of the mass and to mask the flavor of any medicine included therewith. The flavoring is preferably food grade quality. Sweeteners constitute one type of suitable flavoring. Examples of suitable sweeteners include such sugars as xylose, ribose, sucrose, mannose, galactose, fructose, dextrose, and maltose. Other suitable sweeteners include molasses, honey, maple syrup, and fruit flavoring. The sweeteners may be in powdered, granulated, or liquid form. Natural or synthetic sweeteners are suitable. Preferred sweeteners include powdered sugar and dry molasses. Other suitable flavorings include carob, peanuts, garlic, and herbs such as, parsley, celery, peppermint, and spearmint. Natural and synthetic flavoring oils can also be included as a flavoring. Examples of flavoring oils include anise oil, spearmint oil, peppermint oil, cinnamon oil, wintergreen oil, citrus oils, such as lemon, orange, grape, lime, and grapefruit oils. Other suitable flavorings include fruit essences such as apple, strawberry, cherry, and pineapple essences, among others. The flavoring may be included in an amount from about 0.01% to about 20% w/w of the delivery system, such as from about 2% to about 15% w/w or from about 5% to about 10% w/w of the delivery system.

The composition preferably includes an antioxidant. Examples of suitable antioxidants include alpha-tocopherol, alpha-tocopherol acetate, butylated hydroxytoluene (BHT), ascorbic acid, mixed tocopherols, propyl gallate, and mixtures thereof. The antioxidant may be included in an amount from about 0.01% to about 0.3% w/w of the delivery system, such as from about 0.025% to about 0.2% w/w or from about 0.05% to 0.15% w/w.

The composition preferably includes a preservative to prevent or retard growth of microorganisms and fungi. Suitable preservatives include potassium sorbate, methylparaben, propylparaben, sodium benzoate, calcium propionate, or combinations thereof. A preferred preservative comprises a combination of potassium sorbate, methylparaben, and propylparaben. The preservatives may be included in an amount from about 0.01% to about 1% w/w of the delivery system, such as from about 0.03% to about 0.75% w/w or from about 0.05% to about 0.75% w/w of the delivery system.

The composition preferably includes one or more salts comprising mono- and/or divalent cations for proper gelation of the mass. Suitable sources of mono- and divalent cations include sodium, potassium or calcium salts such as sodium chloride, potassium chloride, calcium chloride, or potassium citrate, among others. Such a salt may be included in an amount from about 0.01% to about 5% w/w of the delivery system, such as from about 0.1% to about 2.5% w/w or from about 0.4% to about 0.6% w/w of the delivery system.

The composition preferably includes water in an amount from about 1% to about 50% w/w of the delivery system, such as from about 1% to about 30% w/w or about 5% to about 15% w/w. The composition preferably includes an oil in an amount from about 1% to about 50% w/w of the delivery system, such as from about 1% to about 30% w/w or about 5% to about 15% w/w. Suitable oils include, for example, canola oil, corn oil, soybean oil, and vegetable oil, among others.

The amounts of each of the components in the composition may be varied from the amounts described herein depending upon the nature of the delivery drug, the weight and condition of the animal to be treated, and the unit dosage desired. Those of ordinary skill in the art will be able to adjust dosage amounts as required.

The individual ingredients (e.g., active ingredients and delivery system ingredients) in the soft chew delivery system can be mixed together in a standard mixing apparatus. The dry powders can be mixed initially. This can be followed by the addition of liquid materials to create a soft dough that is easily pliable by hand. The materials are preferably mixed until the dough composition has reached a satisfactory pliability texture level and no dry materials are present. The dough can then be transferred to an extruder device hopper. The extruder device hopper can feed the soft dough through an extrusion port, and a knife blade can chop the extruded dough composition to a desired length and weight. The cut pieces of the invention can subsequently be packaged.

The extruded dough can form any cross-sectional shape depending on the extrusion port design. Suitable shapes include rectangles, squares, circles, triangles, or other specific shapes such as animal or bone shapes. A preferred cross-sectional shape is a thin rectangle. The extruded dough can also have any length, which is determined by the distance between the knife cuts as the dough leaves the extrusion port. The size of the final product may be varied depending on the size of the target animal. In some versions of the invention, the viscoelastic mass takes the form of a sheet, i.e., having a depth less than about half the magnitude of the length and width, such as a depth less than about a quarter the magnitude of the length and width.

The extruded dough can be in any shaped depending on the extrusion port design. These shapes range from a shapeless mass, cylinders, rectangles, squares, circles, triangles, or other specific shapes such as animals or bones shapes.

The compositions of the invention can be use in methods of improving gut health in an animal. The methods comprise orally administering an oral ingestible composition of the invention to the animal. The administering is preferably performed in an amount and for a time effective to improve gut health in the animal. Improvements to gut health can include or be indicated by a reduction of phenols present in the feces of the animal, a reduction of indoles in the feces of the animal, a reduction of mucositis, a reduction of gastroenteritis, or any other indicator or outcome of improved gut health.

The form of the composition administered to the animal can be a soft chew format, a dispersible powder administered as is, a dispersible powder added to a foodstuff prior to administering to the animal, or any other suitable format.

The animal to which the composition is administered can be an animal under stress or exhibiting detectable signs of stress, an animal suffering from gastroenteritis, an animal suffering from mucositis, or any other animal in need of improved gut health. Animals under stress can include animal undergoing travel, showing, training, hunting, breeding, lactation, kenneling, infection, illness, etc. Signs of stress can include excessive drooling, excessive panting, excessive sweating, tucked tail, excessive shedding, nausea, vomiting, diarrhea, constipation, destructive behavior, avoidance behavior, aggression, excessive urinary accidents, ear rotation, and yawning.

The composition can be administered to any animal, including mammals. Non-limiting examples of suitable animals include humans, dogs, cats, horses, cows, pigs, goats, and sheep, among others.

For therapeutic purposes, the composition is preferably administered to the animal in an amount from about 0.006 g/kg animal body weight/day to about 6 g/kg animal body weight/day, such as from about 0.02 g/kg animal body weight/day to about 2 g/kg animal body weight/day or about 0.06 g/kg animal body weight/day to about 0.6 g/kg animal body weight/day. The composition is preferably administered to the animal for a period of at least 1-10 days or more. Exemplary amounts include 1, 2, 3, 4, 5, 6, 7, 8, 9, 10, or more days. The composition is preferably administered daily over the course of the treatment period.

The composition can be generally administered in an amount and for a time to alleviate any one or more of the systems, disorders, or conditions described herein. In some versions, the composition can be administered in an amount and for a time effective to reduce a value of a parameter selected from the group consisting of phenol concentration and indole concentration in the feces of the animal over the course of the treatment. In some versions, the composition can be administered in an amount and for a time effective to reduce a value of a parameter selected from the group consisting of phenol concentration and indole concentration in the feces of the animal with respect to a value of the parameter in the feces of the animal not administered the oral ingestible composition but otherwise subjected to identical conditions.

An amount and a time effective to reduce a value of a parameter selected from the group consisting of phenol concentration and indole concentration in the feces of the animal with respect to a value of the parameter in the feces of the animal not administered the oral ingestible composition but otherwise subjected to identical conditions can be determined for a class of animals using the methods provided in the examples. A reduction of phenol and or indole concentration in an animal is indicative of a reduction of pathogenic bacteria present in the gut of an animal.

It is therefore an object of the invention to provide a simple method of orally administering active ingredients to animals that allow on-going treatment of GI issues such as gastroenteritis and mucositis.

It is a further object of the invention to add beneficial active ingredients in a highly palatable delivery system of a soft chew format or a soft powder format.

A focus of the present invention is the issue of GI disorders due to impaired mucosal barrier function, which is an important cause of GI disorders.

Any version of any component or method step of the invention may be used with any other component or method step of the invention. The elements described herein can be used in any combination whether explicitly described or not.

Any exemplified component described in any embodiment herein can be included in the composition of the invention an amount within a range +/−10-fold or +/−3-fold of the exemplified amount.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure from 1 to 10 should be construed as supporting a range from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

EXAMPLES

Example 1—Soft Chew Delivery System

Ingredients as found in Table 1 were mixed together by first mixing the dry materials in a mixing device followed by mixing in the liquid ingredients to create a soft chew delivery system. The mixing resulted in a soft dough that was extruded through an extrusion device. The dye shape on the extruder resulted in cylinder shaped strands that were cut into 8-gram pieces. The extruded shaped material was packaged.

TABLE 1

Soft Chew Delivery System

| Ingredient | % w/w |
|---|---|
| Soy Flour | 9.80% |
| Soy Lecithin | 8.00% |
| Pregelatinized Starch | 7.00% |
| Dry Molasses | 14.00% |
| Soy Oil | 7.90% |
| Glycerin | 11.00% |
| Poultry Liver Powder | 12.00% |
| Potassium Sorbate | 0.50% |
| Sodium Chloride USP | 0.50% |
| Powder Sugar | 5.00% |
| Mixed Tocopherols | 0.10% |
| Whole Wheat Fine Flour | 15.50% |
| Water | 8.50% |
| Methylparaben | 0.1% |
| Propylparaben | 0.1% |

Example 2—Palatability of Soft Chew Delivery System

Palatability trials were conducted on the soft chew delivery system generated in Example 1. Twenty dogs were given single 8-gram pieces of the delivery system. All of the dogs consumed the composition within 10 seconds. This indicated that the soft chew delivery system was palatable to the dog.

Example 3—Soft Chew Delivery System with Active Ingredients

Active ingredients shown in Table 2 were mixed with soft chew delivery system ingredients on a relative % w/w basis of the total mixture to create 100 lbs. of a composition of the invention. The composition was extruded and cut into 8-gram pieces as described in Example 1. Twenty dogs were given single 8-gram pieces of the composition. All of the dogs consumed the oral dose within 10 seconds. This indicates that the active ingredients for treating gastroenteritis were successfully masked by the soft chew delivery system of the invention.

TABLE 2

Active Ingredients*

| Ingredient | % w/w |
| --- | --- |
| Ascorbic Acid | 0.10% |
| OPTIMIN ® Copper 15% | 0.10% |
| Ferrous Sulfate Monohydrate 30% | 0.10% |
| Bacillus coagulans 200B | 0.30% |
| Inulin | 0.50% |
| Vitamin A 50% WS | 0.10% |
| Vitamin E 50% WS | 0.10% |
| BIOPLUS ® 2B-20 | 1.00% |
| Beta Glucan | 0.25% |
| Sodium Selenite 2.0% | 0.25% |
| L-Arginine HCL | 0.15% |

*OPTIMIN ® Copper 15% (Trouw Nutrition International BV, 5048 AZ Tilburg, The Netherlands) contains a copper amino acid chelate hydrate derived from hydrolyzed soybean protein; contains 15% w/w copper. "200B" refers to the effective amount of viable bacteria, wherein 200B means 200 billion CFU/g. "WS" refers to amount water soluble. BIOPLUS ® 2B-20 (CHR Hansen, Hørsholm, Denmark) is a source of live (viable) Bacillus licheniformis and Bacillus subtilis at 20 billion CFU/gram; composition contains sucrose, sodium silico aluminate, dried Bacillus licheniformis fermentation product and dried Bacillus subtilis fermentation product.

Example 4

The ingredients in Table 3 were mixed together to form a powder formulation. The powder formulation was top dressed onto dog food kibble at a rate of 5 grams powder per 1 kg kibble. This was consumed by a dog without refusal. This indicates the powder formulation is palatable to dogs.

TABLE 3

Powder Formulation*

| Ingredient | % w/w |
| --- | --- |
| Dicalcium Phosphate Anhydrous | 20.00% |
| Ascorbic Acid | 0.10% |
| OPTIMIN ® Copper 15% | 0.10% |
| Ferrous Sulfate Monohydrate 30% | 0.10% |
| Bacillus coagulans 200B | 0.30% |
| Maltodextrin | 41.40% |
| OPTIMIN ® Manganese 15% | 0.10% |
| Poultry Liver Powder | 22.85% |
| Sodium Chloride | 2.00% |
| Powdered Sugar 10X | 8.50% |
| L-Taurine | 0.10% |
| Inulin | 0.50% |
| Vitamin A 50% WS | 0.10% |
| Vitamin E 50% WS | 0.10% |
| BIOPLUS ® 2B-20 | 1.00% |
| TIXOSIL ® | 2.00% |

TABLE 3-continued

Powder Formulation*

| Ingredient | % w/w |
| --- | --- |
| Beta Glucan | 0.25% |
| Sodium Selenite 2.0% | 0.25% |
| L-Arginine HCL | 0.15% |
| OPTIMIN ® Zinc 15% | 0.10% |
| | 100.00% |

*OPTIMIN ® Copper 15% (Trouw Nutrition International BV, 5048 AZ Tilburg, The Netherlands) contains a copper amino acid chelate hydrate derived from hydrolyzed soybean protein; contains 15% w/w copper. "200B" refers to the effective amount of viable bacteria, wherein 200B means 200 billion CFU/g. "WS" refers to amount water soluble. OPTIMIN ® Manganese 15% (Trouw Nutrition International BV, 5048 AZ Tilburg, The Netherlands) is the product resulting from the chelation of a soluble inorganic manganese salt with amino acids and/or partially hydrolyzed protein; contains 15% w/w manganese. BIOPLUS ® 2B-20 (CHR Hansen, Hørsholm, Denmark) is a source of live (viable) Bacillus licheniformis and Bacillus subtilis at 20 billion CFU/gram; composition contains sucrose, sodium silico aluminate, dried Bacillus licheniformis fermentation product and dried Bacillus subtilis fermentation product. TIXOSIL ® (Solvay, Brussels, Belgium) is silica. OPTIMIN ® Zinc 15% (Trouw Nutrition International BV, 5048 AZ Tilburg, The Netherlands) is the product resulting from the chelation of a soluble inorganic zinc salt with amino acids and/or partially hydrolyzed protein; contains 15% w/w zinc.

Example 5

A controlled clinical trial to evaluate the efficacy and safety of the invention was carried out in healthy dogs to measure phenol concentrations in the feces as an indicator of gut health.

Baseline phenol concentrations in the feces of adult beagle dogs were tested prior to treatment. A high protein diet of CESAR® Filet Mignon Pate (Cesar, McLean, Va.) was then given to a control (N=5) group of the adult beagle dogs and a treated (N=5) group of the adult beagle dogs. The CESAR® Filet Mignon Pate given to the treated dogs was top dressed with the powder formulation in Table 3 in an amount effective to deliver a dose of 2 grams of powder formulation/dog/day (0.166 g powder formulation/kg body weight/day) for 10 days. After 10 days the phenol concentrations in feces were again tested.

Fecal phenol concentrations were determined using gas chromatography according to the method of Flickinger et al. (Flickinger et al. 2003) with modifications. Specifically, Thermo Scientific™ TRACE™ 1300 Gas Chromatograph (GC) coupled with Flame Ionization Detector (FID) was used for fecal phenol and indole analysis. Sample volume of 1 µl was injected at 220° C. at splitless mode. Phenolic compounds were separated on a Nukol Supelcol column (60 m length, 0.32 mm diameter) with a film thickness of 0.25 µm. Oven temperature was initially at 150° C., held for 1 min, then increased at 25° C./min to 200° C. and held for 35 min. 5-Methylindole was used as internal standard. Phenols were extracted by mixing 2 g of feces with 5 mL of methanol containing 2,000 ppm of 5-chloroindole (internal standard). The feces-methanol mixture was covered with parafilm, mixed well, and incubated for 1 h at 4° C., with frequent mixing. Tubes then were centrifuged at 29,000×g for 20 min at 4° C. and the supernatant was collected. The remaining pellet was mixed again with 5 mL methanol and extracted as detailed above. The two supernatant fractions were combined for GC analysis.

The results in FIG. 1 show at time zero there were no statistical differences (NS) between the control group and the treated group for phenol concentrations in the feces. At day 10, however, there was a statistically significant difference (*P<0.05) between the control group and the treated group for phenol concentrations in the feces, with the control group showing a lower a lower phenol concentration. The control group showed a showed a statistically significant increase in the phenol concentrations in the feces from day 0 to day 10. There were no adverse clinical reactions noted in any of the treated or control group animals. These results are consistent with the presence of pathogenic bacteria in the control group dogs that are stimulated by the high protein meat diet to produce phenols from L-tyrosine that end up in the feces. The addition of a composition of the invention to the diet reduces the amount of phenols in the feces by reducing the effects of pathogenic bacteria present in the gut of dogs. These results are consistent with the compositions of the invention being efficacious in dogs to produce improved gut health.

Example 6

A controlled clinical trial to evaluate the efficacy and safety of the invention was carried out in healthy dogs to measure indole concentrations in the feces as an indicator of gut health. Baseline indole concentrations in the feces of adult beagle dogs were tested prior to treatment. A high protein diet of CESAR® Filet Mignon Pate (Cesar, McLean, Va.) was then given to a control (N=5) group of the adult beagle dogs and a treated (N=5) group of the adult beagle dogs. The CESAR® Filet Mignon Pate given to the treated dogs was top dressed with the powder formulation in Table 3 in an amount effective to deliver a dose of 2 grams of powder formulation/dog/day (0.166 g powder formulation/kg body weight/day) for 10 days. After 10 days the indole concentrations in feces were again tested.

Indole phenol concentrations were determined using gas chromatography according to the method of Flickinger et al. with modifications. Specifically, Thermo Scientific™ TRACE™ 1300 Gas Chromatograph (GC) coupled with Flame Ionization Detector (FID) was used for Fecal indole analysis. Sample volume of 1 µl was injected at 220° C. at splitless mode. Indole compounds were separated on a Nukol Supelcol column (60 m length, 0.32 mm diameter) with a film thickness of 0.25 µm. Oven temperature was initially at 150° C., held for 1 min, then increased at 25° C./min to 200° C. and held for 35 min. 5-methylindole was used as internal standard. Indoles were extracted by mixing 2 g of feces with 5 mL of methanol containing 2,000 ppm of 5-chloroindole (internal standard). The feces-methanol mixture was covered with parafilm, mixed well, and incubated for 1 h at 4° C., with frequent mixing. Tubes then were centrifuged at 29,000×g for 20 min at 4° C. and the supernatant was collected. The remaining pellet was mixed again with 5 mL methanol and extracted as detailed above. The two supernatant fractions were combined for GC analysis.

Figure 2:
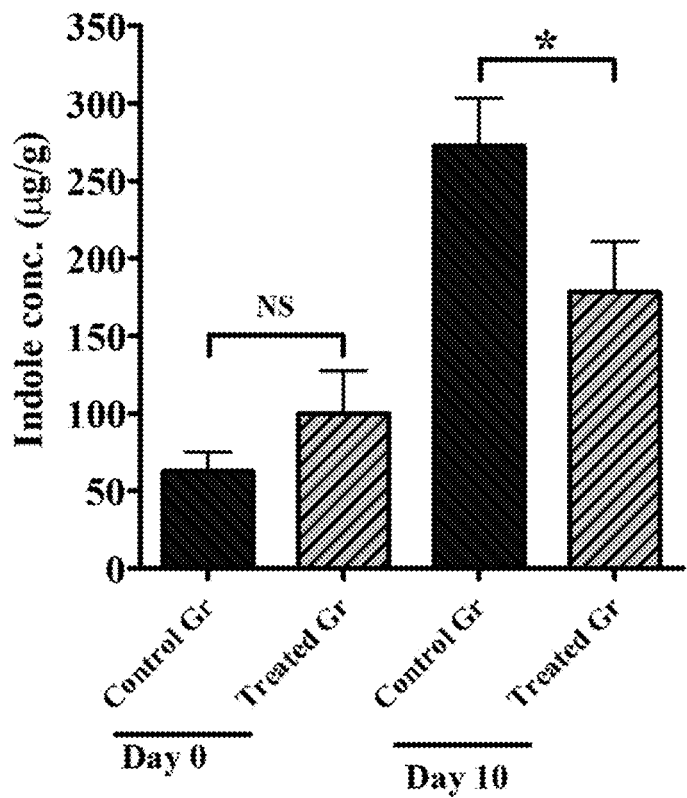
FIG. 2 shows indole concentrations at days 0 and 10 in the feces of animals fed a high-protein control diet and animals fed a high-protein diet supplemented with a composition of the invention.

The results in FIG. 2 show at time zero there were no statistical differences (NS) between the control group and the treated group for indole concentrations in the feces. At day 10, however, there was a statistically significant difference (*P<0.05) between the control group and the treated group for indole concentrations in the feces, with the control group showing a lower a lower indole concentration. The control group showed a showed a statistically significant increase in the indole concentrations in the feces from day 0 to day 10. These results are consistent with the presence of pathogenic bacteria in the control group dogs that are stimulated by the diet to produce indoles that end up in the feces. The addition of a composition of the invention to the diet reduces the amount of indoles in the feces by reducing the effects of pathogenic bacteria present in the gut of dogs.

These results are consistent with the compositions of the invention being efficacious in dogs to produce improved gut health.

REFERENCES

Blijlevens N M, Richard M. Logan and Mihai G. Netea Mucositis: from febrile neutropenia to febrile mucositis. *Journal of Antimicrobial Chemotherapy* (2009) 63, Suppl. 1, i36-i40.

Flickinger E A, Schreijen E M W C, Patil A R, Hussein H S, Grieshop C M, Merchen N R, and Fahey Jr. G C. "Nutrient digestibilities, microbial populations, and protein catabolites as affected by fructan supplementation of dog diets." *Journal of Animal Science* 81 (2003): 2008-2018.

Herstad H K, Nesheim B B, L'Abée-Lund T, Larsen S, Skancke E. Effects of a probiotic intervention in acute canine gastroenteritis—a controlled clinical trial. *J Small Anim Pract.* 2010 January; 51(1):34-8.

Kochar N I, Sudhir N Umathe. Beneficial effects of L-arginine against diabetes-induced oxidative stress in gastrointestinal tissues in rats. *Pharmacol Rep*, Volume 2009; 61(4): 665-672.

Kochar N I, Anil V. Chandewal, Ravindra L. Bakal and Priya N. Kochar, 2011. Nitric Oxide and the Gastrointestinal Tract. *International Journal of Pharmacology*, 7: 31-39.

Kogut M H. The gut microbiota and host innate immunity: Regulators of host metabolism and metabolic diseases in poultry? 2013 J. *Appl. Poult. Res.* 22:637-646.

Leocádio P C, Antunes M M, Teixeira L G, Leonel A J, Alvarez-Leite J I, Machado D C, Generoso S V, Cardoso V N, Correia M I. L-arginine pretreatment reduces intestinal mucositis as induced by 5-F U in mice. *Nutr Cancer.* 2015; 67(3):486-93.

Mansourian S., Corcoran J. et al. Fecal-derived phenol induces egg-laying aversion in Drosophila. *Current Biology* 2016, 26, 2760-2768.

Popovic P J, Herbert J. Zeh III, and Juan B. Ochoa. Arginine and Immunity. *J. Nutr.* 137: 1681S-1686S, 2007.

Rishi P, Bharrhan S, Singh G, Kaur P. Effect of *Lactobacillus plantarum* and L-arginine against endotoxin-induced liver injury in a rat model. Life Sci. 2011 Dec. 5; 89(23-24): 847-53

Raul F, Galluser M, Schleiffer R, Gosse F, Hasselmann M, Seiler N. Beneficial effects of L-arginine on intestinal epithelial restitution after ischemic damage in rats. *Digestion* 1995; 56(5):400-5.

Sauter, S. N., Benyacoub, J., Allenspach, K., Gaschen, F., Ontsouka, E., Reuteler, G., Cavadini, C., Knorr, R. & Blum, J. W. (2006) Effects of probiotic bacteria in dogs with food responsive diarrhea treated with an elimination diet. *Journal of Animal Physiology and Animal Nutrition* 90, 269-277.

Suzuki H., Watabe J., Takeuchi H., Tadano Y., Matsuda S., Murata K. 2004. Effect of *Bacillus subtilis* C-3102 intakes on the composition and metabolic activity of fecal microflora of humans. *J. Intestinal. Microbiol.* 18: 93-99.

Ishisaki S. Matusuda A. et al. Oral Administration of Fermented Probiotics Improves the Condition of Feces in Adult Horses. *J. Equine Sci.* 2014; 25(4): 65-72.

Umathea, S N, N. I. Kochara, N. S. Jainb, P. V. Dixit. Gastrointestinal dysfunction in diabetic rats relates with a decline in tissue 1-arginine content and consequent low levels of nitric oxide. *Nitric Oxide* Volume 20, Issue 2, 1 Mar. 2009, Pages 129-133.

Wang Z Q, Rachel J. Lawson, Madhavan R. Buddha, Chin-Chuan Wei, Brian R. Crane, Andrew W. Munro, and Dennis J. Stuehr. Bacterial Flavodoxins Support Nitric Oxide Production by *Bacillus subtilis* Nitric-oxide Synthase. *Journal of Biological Chemistry* 282:2196, 2007.

Wapnir R A, M A Wingertzahn, S Teichberg L-arginine in low concentration improves rat intestinal water and sodium absorption from oral rehydration solutions. *Gut* 1997; 40: 602-607.

What is claimed is:

1. A method of improving gut health in an animal, the method comprising orally administering to an animal in need thereof a therapeutically effective amount of an oral ingestible composition, wherein: the composition comprises effective amounts of active ingredients; and the active ingredients comprise a probiotic and a nitric oxide precursor, and wherein the probiotic comprises *Bacillus coagulans* or *Bacillus licheniformis*.

2. The method of claim 1, wherein the probiotic comprises a combination of *Bacillus coagulans, Bacillus licheniformis*, and *Bacillus subtilis*.

3. The method of claim 1, wherein the probiotic is included in the composition in an amount from about 0.15% w/w to about 15% w/w.

4. The method of claim 1, wherein the nitric oxide precursor comprises L-arginine.

5. The method of claim 1, wherein the nitric oxide precursor is included in the composition in an amount from about 0.015% w/w to about 1.5% w/w.

6. The method of claim 1, wherein the oral ingestible composition further comprises beta glucan.

7. The method of claim 1, wherein the oral ingestible composition further comprises vitamin C, vitamin A, and vitamin E.

8. The method of claim 1, wherein the oral ingestible composition further comprises a prebiotic.

9. The method of claim 1, wherein the oral ingestible composition is in the form of a soft dough composition with the active ingredients evenly distributed throughout.

10. The method of claim 1, wherein the oral ingestible composition is in the form of a dispersible powder.

11. The method of claim 1, wherein the oral ingestible composition is in the form of a dispersible powder and is added to a foodstuff prior to the administering.

12. The method of claim 11, wherein the foodstuff is a solid foodstuff.

13. The method of claim 1, wherein the animal is an animal exhibiting detectable signs of stress.

14. The method of claim 1, wherein the animal is an animal suffering from gastroenteritis.

15. The method of claim 1, wherein the animal is an animal suffering from mucositis.

16. The method of claim 1, wherein:
the nitric oxide precursor is L-arginine and is included in the composition in an amount from about 0.015% w/w to about 1.5% w/w;
the probiotic is included in the composition in an amount from about 0.15% w/w to about 15% w/w; and
the composition is administered to the animal in an amount from about 0.02 g/kg animal body weight/day to about 2 g/kg animal body weight/day for a period of at least two consecutive days.

17. The method of claim 1, wherein the composition is administered in an amount and for a time effective to reduce a value of a parameter selected from the group consisting of phenol concentration and indole concentration in feces of the animal with respect to a value of the parameter in the feces of the animal not administered the oral ingestible composition but otherwise subjected to identical conditions.

* * * * *